US00PP34724P2

(12) United States Plant Patent
Azwell et al.

(10) Patent No.: US PP34,724 P2
(45) Date of Patent: Nov. 8, 2022

(54) HEMP PLANT NAMED 'NACL'

(50) Latin Name: ***Cannabis* spp.**
Varietal Denomination: NaCl

(71) Applicant: GeneticsCubed, LLC, Hurricane, UT (US)

(72) Inventors: Thomas Azwell, Berkeley, CA (US); Arthur Adams, Stockton, CA (US)

( * ) Notice: Subject to any disclaimer, the term of this patent is extended or adjusted under 35 U.S.C. 154(b) by 0 days.

(21) Appl. No.: 17/490,902

(22) Filed: Sep. 30, 2021

(51) Int. Cl.
*A01H 5/12* (2018.01)
*A01H 6/28* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
(74) *Attorney, Agent, or Firm* — David R. Conklin; Kirton McConkie

(57) ABSTRACT

The present invention provides a new and distinct variety of hemp designated as 'NaCl', which has improved resilience to high salinity soil and drought conditions, as well as tolerance to small rootzone conditions.

8 Drawing Sheets

Latin name of the genus and species of the plant claimed: *Cannabis* spp.

Variety denomination: 'NaCl'.

BACKGROUND OF THE INVENTION

*Cannabis* is the genus of a variety of species—*Cannabis sativa, Cannabis ruderalis,* and *Cannabis indica*—which is often used as an umbrella term to refer to them all. This misclassification of the different species has made it difficult to properly distinguish between and understand the best ways to utilize the different varieties of these plants.

According to the 2018 Farm Bill, Hemp is a variety of *Cannabis sativa* that is distinguished by its low tetrahydrocannabinol (THC) levels of less than 0.3%. THC is the only currently known psychoactive compound found in *Cannabis*, however there are many additional cannabinoid compounds that can be utilized in a variety of ways. The exact concentration results based on lab testing of dried flowers will vary depending on growing conditions of the plant, and sampling, preparation, and testing methods used. THC production, for example, is a natural, chemical defense mechanism for the plant, meaning in high stress or threatening environments the specific plant will produce higher levels of THC. Because of this inconsistency, many state labs are allowing slightly higher levels of THC in the tests as anything under 1% THC has not been proven to have psychoactive effects.

For the purpose of this study on 'NaCl', the cannabinoid percentages are recorded based on a plant grown in a high-stress environment to determine the maximum concentration of THC that will be produced by this specific strain. The results conclude that the 'NaCl' is a type-III hemp cultivar meaning it does not possess the allele to ever make more than 1% THC (and thus is not suitable for marijuana use). Additionally, 'NaCl' is a new, unique variety because it was developed to be a salt tolerant strain and was tested by growing in high salinity, high clay soil with less than optimal nutrient levels and was irrigated with water that had a 300 PPM saline content.

With the recent legalization of hemp in 2018, farmers across the country decided to either convert their old crops or start new fields to grow the more lucrative hemp. In many cases, these farms were established in areas where the soil is less than ideal for hemp. One of the conditions commonly seen is high salinity soil. Having too much salt can cause a number of problems for the plant including but not limited to stunting plant growth, burning root and leaf tips, and blocking uptake of essential nutrients and minerals each of which puts strain on the plants and may even lead to death. Additionally, the environment created by high salinity soil often adds stress to the hemp plants growing in it which creates the risk of increasing THC levels. THC production in *Cannabis* is a chemical defense mechanism that will be more induced when the plant is grown in less than optimal conditions, experiences competition from pests or weeds, or is subject to too much or too little water, among a number of other stress inducing factors. With the current limited industry regulation and support for farmers, too much salt may destroy their entire crop either directly due to plant death, or indirectly due to testing hot (above 0.3% THC). In either case, it is important for farmers with high salt content in their soil to have a strain that will stay consistent and thrive in these conditions.

'NaCl' was developed in a selective breeding program by performing controlled fertilization of known, high-performing hemp varieties. The purpose of the research was to determine what specific cultivars would be able to complete its life cycle with minimal stress in high salinity soil while maintaining a consistent high CBD and low THC profile. The mother was selected from one of ten cultivars grown on a high salt farm in Sonoma County, Calif. The mother was selected because it showed the most resistance to the soil conditions and still maintained its cannabinoid ratio as compared with its clone grown indoors in controlled conditions. The mother was then crossed with twenty different fathers to determine which would carry the salt tolerant trait and consistent cannabinoid levels or even improve upon it. From the seeds produced, 250 of each cultivar was germinated and planted on the high salt farm in Sonoma County. 'NaCl' was selected as the best phenotype of the 5,000 plants grown because of its improved resilience to the soil and impressive cannabinoid profile. Additionally, when grown indoors 'NaCl' showed resistance to being rootbound and is very hardy in most growing environments, making it a great plant for potentially stress inducing environments. The father that was chosen was a feminized father developed inhouse, which means it was a female plant that was induced to produce pollen sacs in place of typical female buds. The creation of pollen by a female meant that crossing a feminized father with a non-feminized mother would yield 100% feminized plants, meaning they will produce female flowers, because only XX chromosomes were crossed. In addition to its resilience and robust cannabinoid profile, 'NaCl' was developed to be feminized so, even when grown from seeds, will be a female plant and produce flower, reducing the risk of a farmer to accidentally pollinate their crop or for pollen drift to affect surrounding farms.

BRIEF SUMMARY OF THE INVENTION

This invention relates to a new and distinctive hemp cultivar designated as 'NaCl'. The distinguishing characteristic of the plant being that it thrives in soil that has high levels of salt where conventional hemp plants would be adversely affected.

As used herein, the term "cultivar" is used interchangeably with the terms "variety," strain," and/or "clone."

Progenies have been reproduced asexually via apical stem cuttings from vegetative plants.

BRIEF DESCRIPTION OF THE DRAWINGS

The accompanying photographs illustrate the new hemp variety.

DETAILED BOTANICAL DESCRIPTION

Figure 1A:
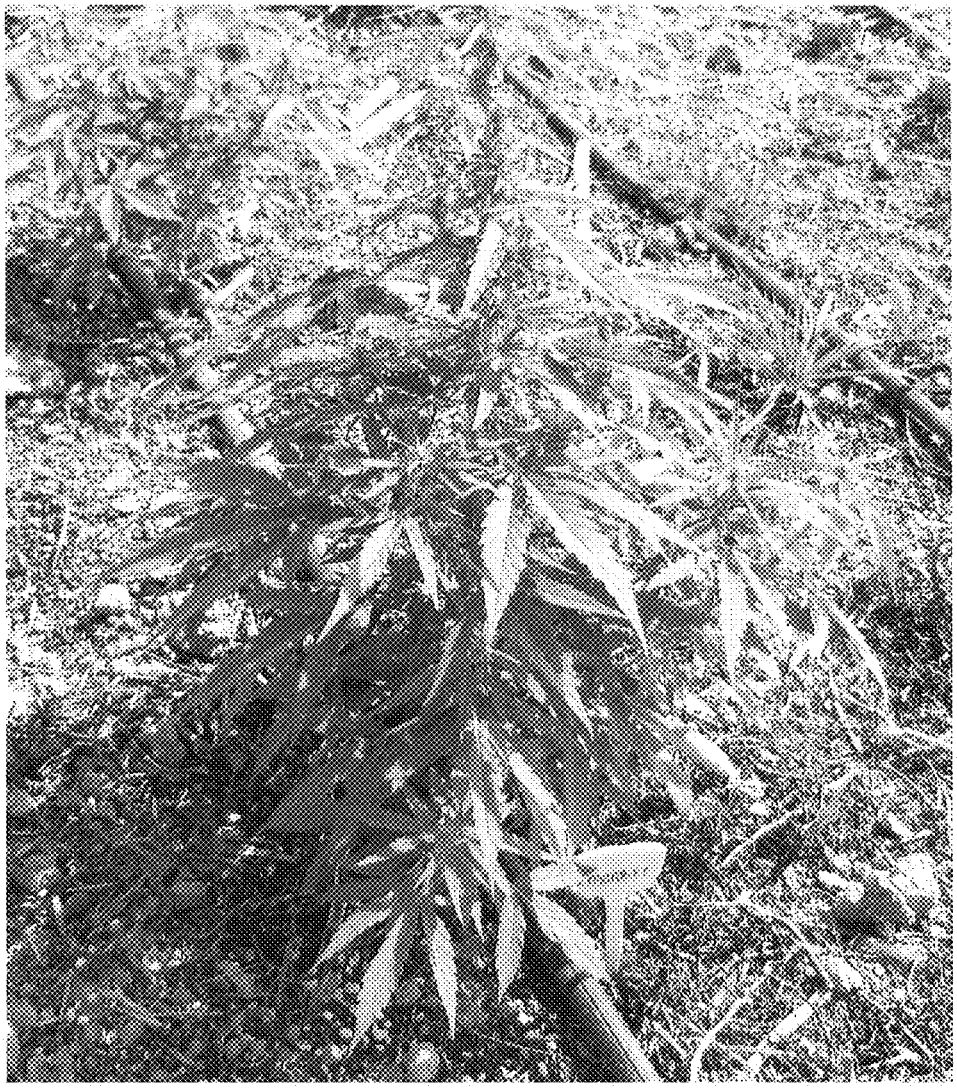
FIGS. 1A and 1B shows perspective views of 'NaCl' seedlings planted outdoors exhibiting vigorous flower growth once flowering began with more lateral growth following the vegetative growth focused on branching.
Figure 1B:
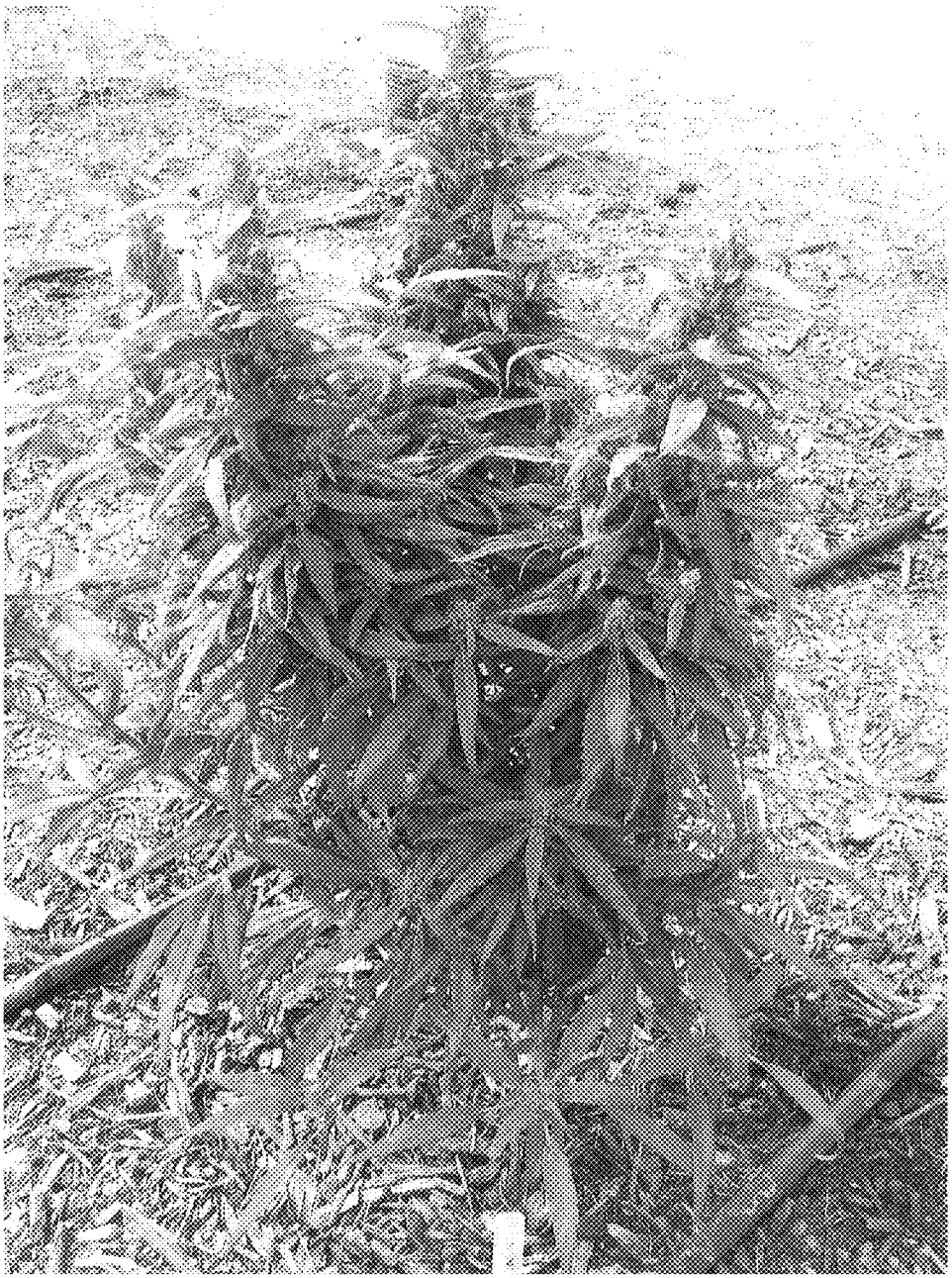
Figure 2:
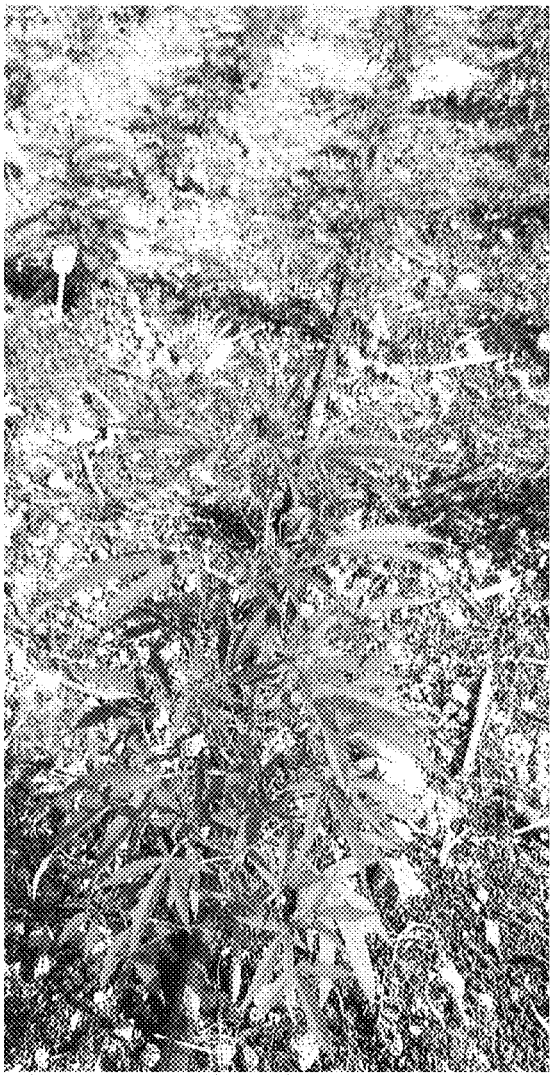
FIG. 2 shows a perspective view of 'NaCl' on a high salinity test plot next to other phenotypes (sisters) as well as inferior genotypes (different strains).
Figure 3:
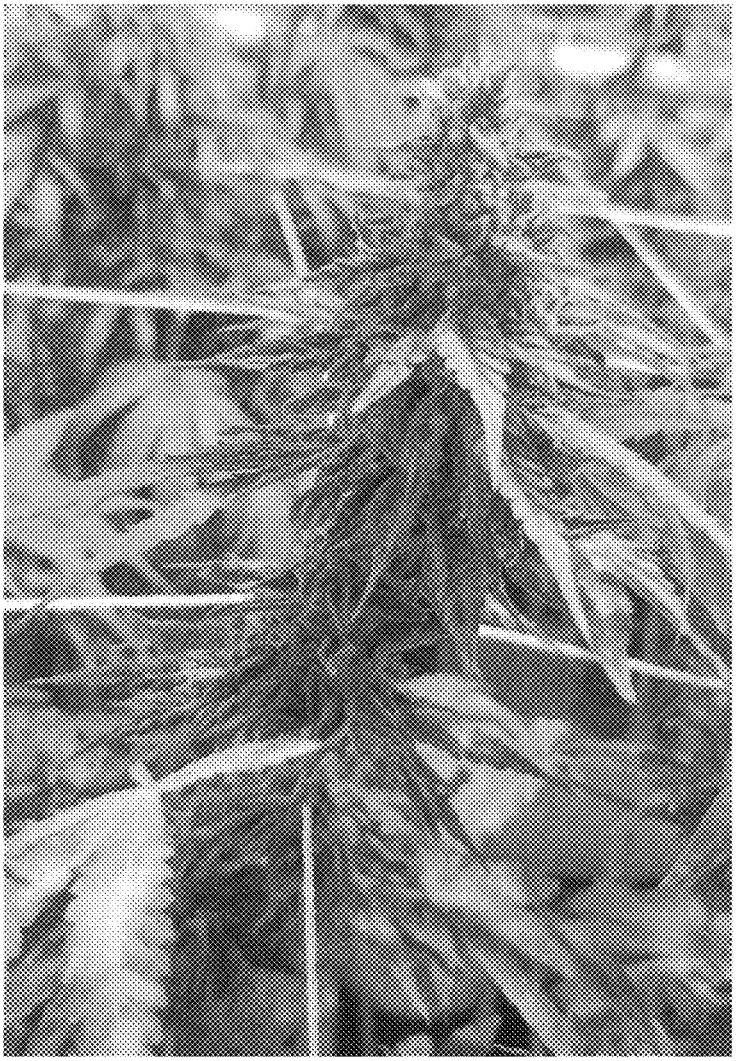
FIG. 3 shows a detailed perspective view of the top of 'NaCl' grown indoors (two weeks prior to harvest)
Figure 4B:
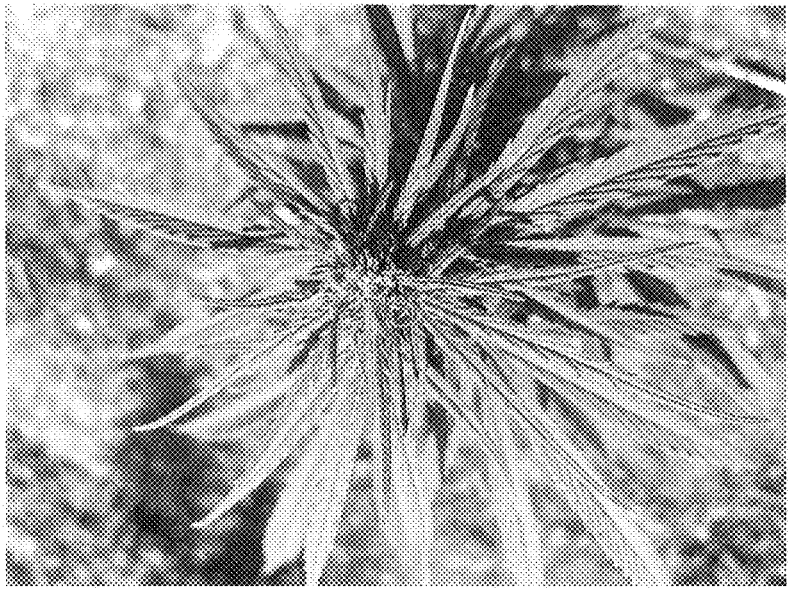
FIGS. 4A and 4B show detailed perspective views of the top of 'NaCl' grown outdoors (four weeks prior to harvest)
Figure 4A:
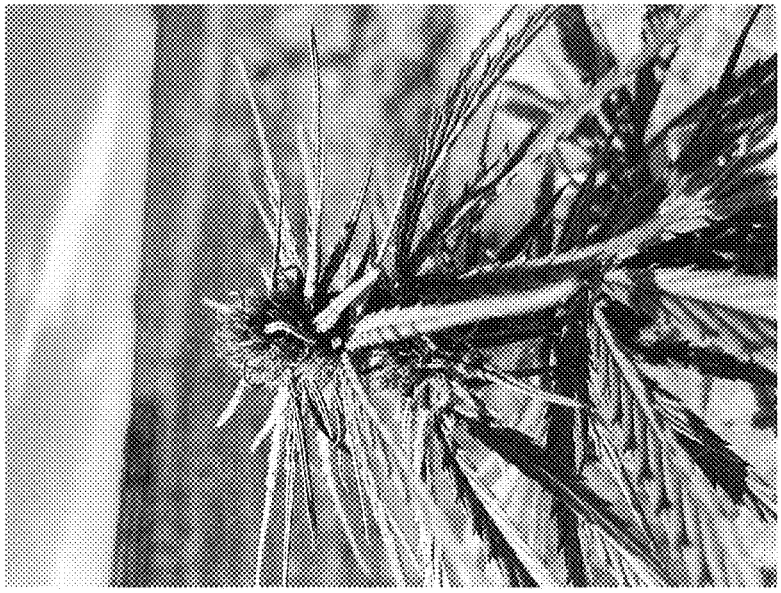
Figure 5B:
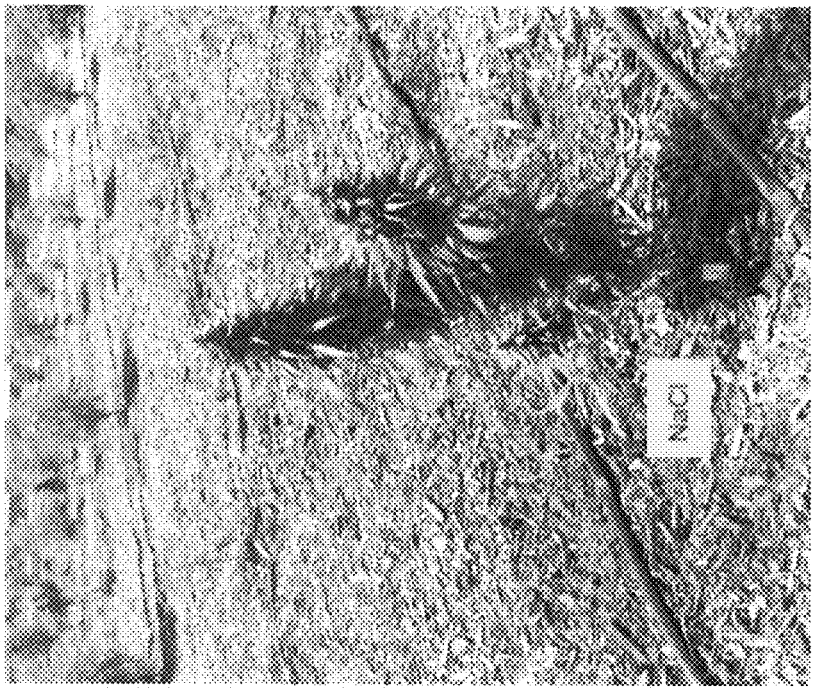
FIGS. 5A-5E show perspective views of 'NaCl' on a high salinity test plot next to other genotypes (different strains).
Figure 5A:
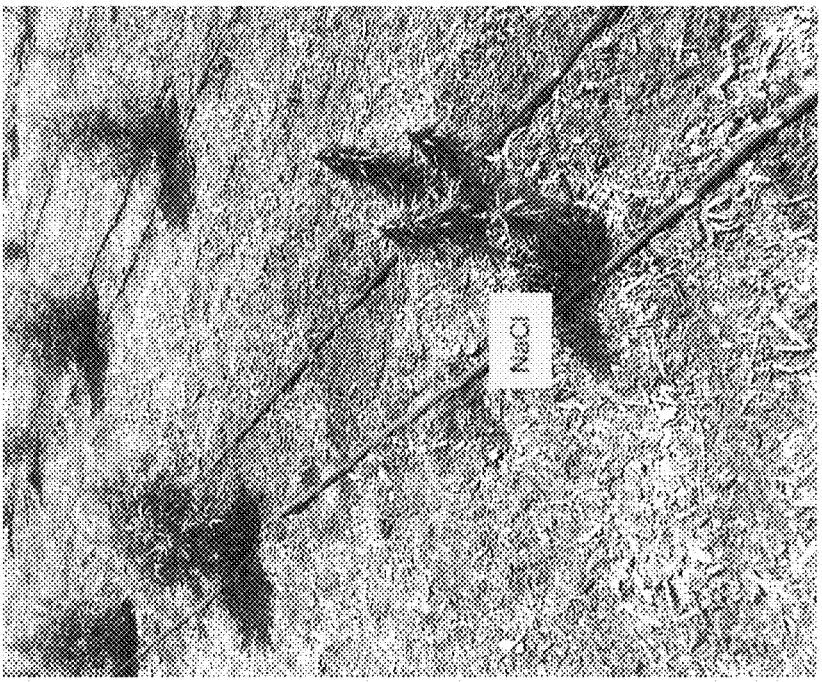
Figure 5C:
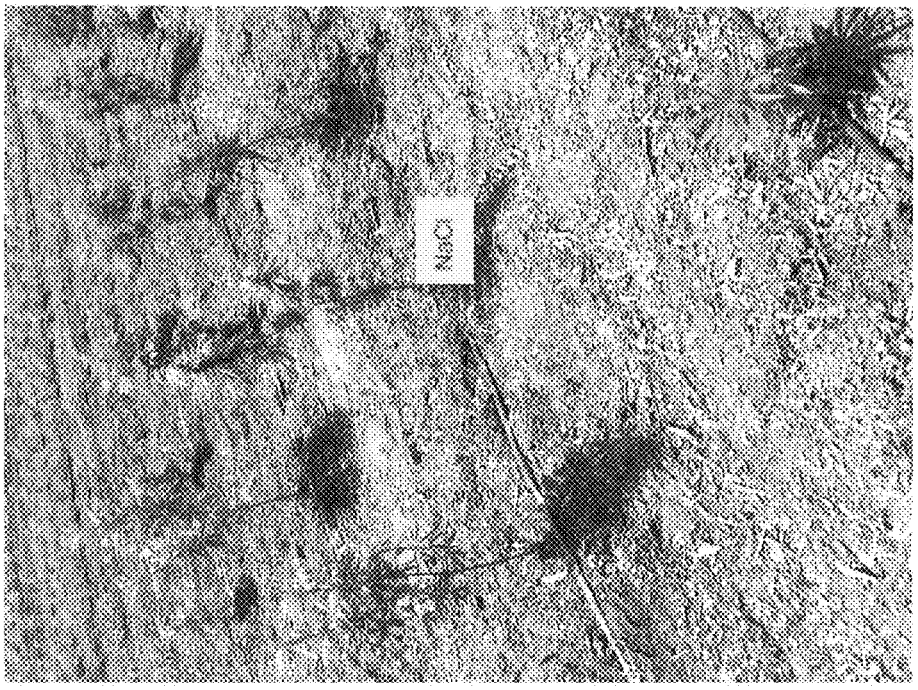
Figure 5D:
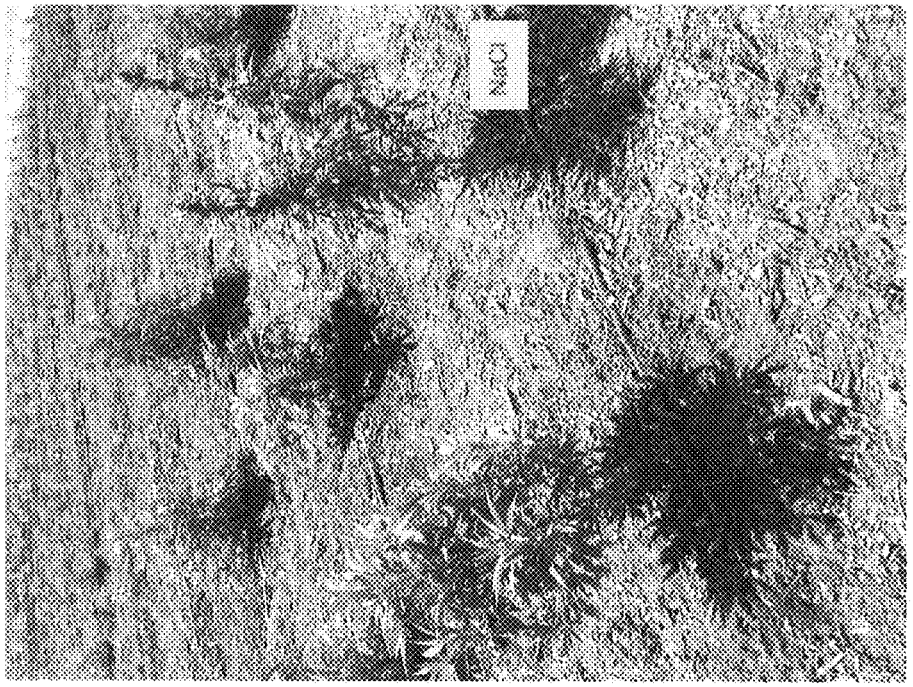
Figure 5E:
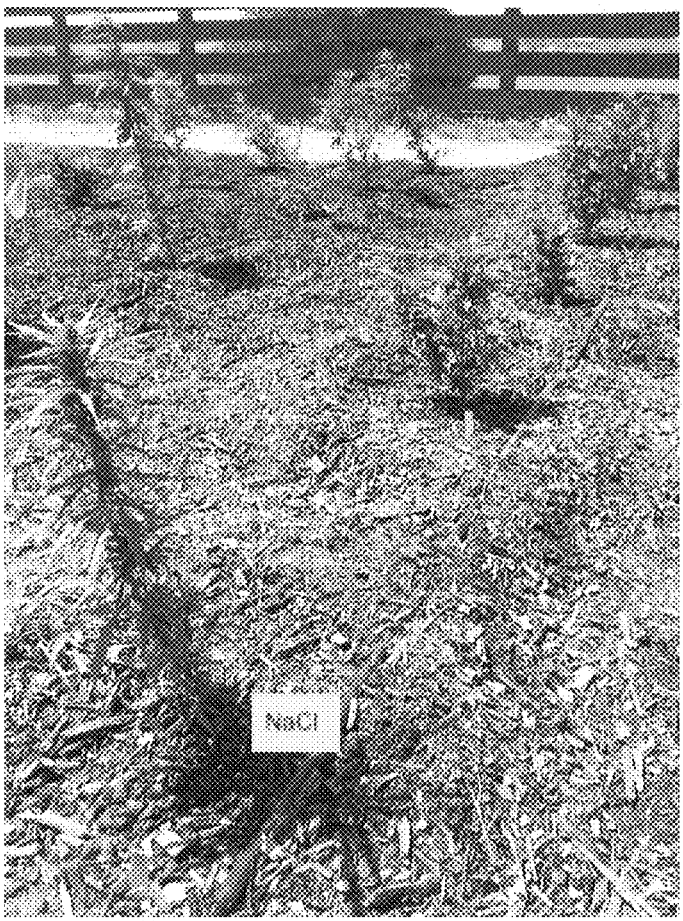

'NaCl' has been examined in manipulated conditions grown both indoors and outdoors. For the purpose of developmental research, 'NaCl' was grown outdoors in high salinity soil to test resilience and cloned indoors in a controlled environment to monitor and ensure stabilized genetics. The variety has not been grown in all possible conditions, thus different environmental factors alter the appearance or composition of this phenotype. The individual has been reproduced asexually via apical stem cuttings from vegetative plants in Sonoma, Calif. Additionally, 'NaCl' has a stable seed line and remains stable and reproduces true to type in successive generations of asexual reproduction.

In the following description, the color determination is in accordance with The Royal Horticultural Society Colour Charts, Fifth Edition, except where general color terms of ordinary dictionary significance are used. Note that variation in color for the same plant on the leaves and stalks can be a result of different nutrient formulas and different amounts of watering. Coloration should only be used as a general picture rather than the distinguishing features. Additionally, length and size of plant parts is dependent on zone, length of growth season, space, and nutrients so may vary between plants.

TABLE I

| General | |
|---|---|
| Characteristics | New Variety ('NaCl') |
| Plant Type | Herbaceous plant (herb) |
| Plant Growth Habit | Upright, dioecious, annual, no hermaphrodite, or monoecious tendencies without stress conditions |
| Plant origin | 'NaCl' was created in a selective breeding program from a cross between the Mother, CC, hemp variety and the Feminized Father, G, hemp variety. |
| Plant Propagation | Asexually reproduced via apical stem cutting and cloning from mother in vegetative state. |
| Propagation ease | Easy |
| Propagation Condition | 80° F., 90% humidity, for 1 week |
| Height (unit: feet) | Outdoors may reach 8-10 feet at maturity<br>Indoors may reach 3-5 feet at maturity depending on growth conditions |
| Width (unit: feet) | Dependent on zone, length of growth season.<br>Outdoors may reach 6-8 feet at maturity<br>Indoors may reach 2 feet depending on growth conditions<br>This plant generally grows round naturally, with strong vertical and lateral branching. |
| Time to Harvest | 60 Days from Induction of flowering light cycle |
| Resistance to Pests or disease | May be susceptible to Podosphaera macularis (Powdery Mildew)<br>Resistance to high salt conditions and some adverse soil conditions (high clay and alkaline).<br>Exhibits resistance to *Tetranychu surticae* (Mite), *Myzus persicae* (Green Peach Aphid), *Phorodon cannabis* (Bhang Aphid), *Myzus persicae* (Green Peach Aphid), and *Aphis fabae* (Black Bean Aphid). |
| Genetically Modified Organism? | No |
| Characteristics | Parental Variety (CC) (Female Plant) |
| Plant Type | Herbaceous plant (herb) |
| Plant Growth Habit | Upright, dioecious, annual, no hermaphrodite or monoecious tendencies without stress conditions |
| Plant origin | Origin unknown |
| Plant Propagation | Asexually reproduced via apical stem cutting and cloning from mother in vegetative state |
| Propagation ease | Easy |
| Propagation Condition | 80° F., 90% humidity |

TABLE I-continued

| General | |
|---|---|
| Height (unit: feet) | Outdoors may reach 8-10 feet at maturity<br>Indoors, may reach 3-4 feet depending on growth conditions |
| Width (unit: feet) | Outdoors may reach 6-8 feet<br>Indoors may reach 1-2 feet |
| Time to Harvest | 60 Days from Induction of flowering light cycle |
| Resistance to Pests or disease | More prone to *Podosphaera macularis* (Powdery Mildew). |
| Genetically Modified Organism? | No |

TABLE II

| Leaf/Foliage | |
|---|---|
| Characteristics | New Variety ('NaCl') |
| Leaf Arrangement | Spiral alternate leaf arrangement when grown from clones. Seedlings will initially have leaf and branching that appears opposite at first and progresses to a more spiral alternate as the plant grows more. The nodes will still have a small internode, followed by a larger internode then another small one, repeated with the small internodes increasing in size higher up on the plant in the newer growth. |
| Leaf Shape | Palmately compound with 7-9 leaflets in mature growth. |
| Leaf Structure | Serrated margins with long, slender lanceolate leaflets. Apex is acuminate but narrows enough to almost be aristate and the base is acuminate. Overall the leaflets are long and slender with even tapering from the middle of the leaflets. |
| Leaf Margins | Serrated margins with both the inner and outer sides of the serration more convex. The tip of the serration slightly curls and angles up to have a more accentuated point that points towards the apex and ended points perpendicularly up from the top of the leaf. Some of the teeth are doubly serrated. |
| Leaf Hairs | Absent |
| Leaf Length with Petiole at Maturity | 12-17 cm |
| Petiole Length at Maturity | 3-6 cm |
| Petiole Color (RHS Number) | 149B |
| Anthocyanin color and intensity in Petioles | Slightly present on top of the petiole closer to the leaflet node. |
| Stipule length at maturity | 3-9 mm |
| Stipule shape | Very slender, almost lance shaped but with a slightly broader base that makes it appear more triangular with a tapering, acuminate apex. |
| Stipule Color (RHS Number) | 149B |

TABLE II-continued

| Leaf/Foliage | |
|---|---|
| Number of Leaflets | 5-9 throughout life cycle |
| Middle Largest (longest leaflet) length | 8-12 cm |
| Middle Largest (longest leaflet) width | 1.5-3 cm |
| Middle Largest (longest Leaflet) length:width Ratio | About 5:1 to 4:1 |
| Number of teeth of middle leaflet | 34-42 |
| Leaf (upper side) color (RHS Number) | 141B to 134A |
| Leaf (lower side) color (RHS Number) | 142A to 142B |
| Leaf Glossiness | Not glossy, bottom and top are matte |
| Vein/midrib shape | Mid veins branch palmately with the leaflets. 2° veins branch pinnately from midveins towards the serration apex and are parallel to one another with minimal curve. The 3° slightly branch pinnately from midvein between the 2° veins and from the 2° veins. Some 3° go towards the margin indent between the serrations; only these and coming off mid-veins are visible from bottom. Indentation of 1° and 2° veins can be seen from the top. |
| Vein/midrib color (RHS Number) | 149B |
| Aroma | Mature buds smell like Pepper and Fruit wine. |

| Characteristics | Parental Variety (CC) (Female Plant) |
|---|---|
| Leaf Arrangement | Spirally alternate when grown from a cutting. Stalk alternates directions back and forth between branches. |
| Leaf Shape | Palmately compound with 5-7 leaflets throughout the life cycle. |
| Leaf Structure | Serrated margins. Elliptical leaf with tapering base and apex. Middle section of leaflets are wide. |
| Leaf Margins | Evenly serrated. Point of serration is more acuminate/tapering to a point. Inner and outer sides of serrations are convex. |
| Leaf Hairs | Absent |
| Leaf Length with Petiole at Maturity | 13.1-19 cm |
| Petiole Length at Maturity | 3.5-5cm |
| Petiole Color (RHS Number) | 150A |
| Anthocyanin color and intensity in Petioles | Purple to green |
| Stipule length at maturity | 1.5-3 mm |
| Stipule shape | Very small, lance shape. Broad/rounded base with acuminate/long tapering apex. |
| Stipule Color (RHS Number) | 150A |

TABLE II-continued

| Leaf/Foliage | |
|---|---|
| Number of Leaflets | 5 to 7 throughout life cycle |
| Middle Largest (longest leaflet) length | 9.3-13 cm |
| Middle Largest (longest leaflet) width | 2-4 cm |
| Middle Largest (longest Leaflet) length:width Ratio | About 4:1 |
| Number of teeth of middle leaflet | 23-25 |
| Leaf (upper side) color (RHS Number) | N144C |
| Leaf (lower side) color (RHS Number) | 149B |
| Leaf Glossiness | Bottom is matte, top has slight light reflection but not shiny |
| Vein/midrib shape | Midvein is palmate with leaflets. 2° veins are pinnate and straight. 3° are also palmate and branch from 1° and 2° veins. All three types are slightly visible from the top. |
| Vein/midrib color (RHS Number) | 149C |
| Aroma | Spicy pepper with a sweet floral aroma. |

TABLE III

| Stem | |
|---|---|
| Characteristics | New Variety ('NaCl') |
| Stem Shape | Has slightly angular ridges throughout the length of the plant, but not furrowed with indentations as some strains are. The stalks grow very parallel and straight up with minimal bending even with heavy flowers. Newer growth has more ridges (~7-8) while old growth has fewer (~4-5). |
| Stem Diameter at Base | 2-13 cm |
| Stem Color | 149A to 150A |
| Stem Pith Type | Thick to woody |
| Stem Internode Length | 2.5-4.0 cm |
| Characteristics | Parental Variety (CC) (Female Plant) |
| Stem Shape | At maturity, round and in the bottom/trunk of the plant, growth appears woody. Immature or new growth has ridges, approximately pentagonal in shape. Between nodes, the stem angles slightly to give a zig-zag appearance. |
| Stem Diameter at Base | 3-12 cm |
| Stem Color | 144A to 146A |
| Stem Pith Type | Moderate to thick |
| Stem Internode Length | 2.5-4.0 cm |

TABLE IV

| Inflorescence | |
|---|---|
| Characteristics | New Variety ('NaCl') |
| Flowering (blooming) habit | Dioecious, but only has female flowers. Large flower:leaf ratio. Having robust flowers on every branch. Flowers are more spread out near the base of the stems and become more clustered and overlapping near the terminal ends of the branches. The leaves are prominent at the base of each flower but are much less apparent as the flower grows, leaving mostly buds. |
| Proportion of female plants | Around 100%, very stable dioecious when grown from regular seed so only has female characteristics |
| Inflorescence Position | Above branches at nodes. Slight pedicles allow the flowers to grow more above the flower and not be hindered by the location of the stem intruding on the bud formation. Pedicles are smaller or less prominent near the terminal ends of the branches where flowers grow closer together. |
| Flower arrangement | Overlapping, congested, individual flowers grow in clumps along branches. Flowers are stacked or clustered at maturity much more prominently near the terminal end of the branches and slightly more spread out centrally on the branches. |
| Number of Flowers per plant | Hundreds to thousands per plant. |
| Flower shape | Minimal symmetry, some buds grow clustered and appear to have multiple apexes on one flower. The entire flower is generally more cylindrical with robust growth from the base up but tapers near the apex to create a conical top. The base of the flower has more fan leaves radiating around it and as the bud begins to narrow, there are few to no leaves present. |
| Flower (individual pistillate) length | 5-10 mm |
| Flower (compound cyme) diameter | 3-13 cm |
| Corolla | No defined corolla. |
| Corolla Color (RHS number) | N/A |
| Bract shape | Small, ovate with tapering apex. Difficult to locate because buds are broader and so are the bracts to cover. |
| Bract color (RHS number) | 144B |
| Bracteole shape (general description) | Same as bract. More within the flower cluster. Hard to identify without dissection. |
| Bracteole color (RHS number) | 144B |
| Calyx Shape (general description) | N/A |
| Calyx color (RHS number) | N/A |

TABLE IV-continued

| Inflorescence | |
|---|---|
| Stigma shape | Ovate shape with long tapering apex where 2 spindle-like styles protrude. |
| Stigma length | 2-6 mm |
| Stigma color (RHS number) | Newly emerged, they are milky white with a slight greenish hue. |
| Trichome shape | Capitate stalked gland, long stalk with smaller bulb on top. In mature plants grow on flowers and leaves. |
| Cystolithic non-glandular | On leaves farther from bud. Leaves grow trichomes that appear glandular when surrounding the flowers. |
| Trichome color (RHS number) | Opaque, white, creamy color (#145D) but changes from clear translucent to slight auburn translucent with maturity/when ready to harvest. |
| Terminal Bud shape | Terminal bud is more symmetrical due to less obstruction from stem. In general, flower is generally more cylindrical from the base up with a relatively consistent diameter until the apex of the bud that begins to narrow. Terminal buds are slightly longer that inner buds. |
| Terminal Bud color (RHS number) | Est. 144A to 144B |
| Pedicle | Present in varying lengths depending on maturity and location of bud |
| Staminate shape | N/A |
| Sepal color (RHS number) | N/A |
| Pollen description | N/A |
| Seed description | Light brown, oval, solitary, 3-7 mm in length. Typically weigh .01-.03 g. Variation observed due to environmental conditions. white lines that look like veins between some of the vertical lines. |
| Marbling of seed | Minimal. |
| Petal description | N/A, Apetalous |

| Characteristics | Parental Variety (CC) (Female Plant) |
|---|---|
| Flowering (blooming) habit | Dioecious, so grows pistillate flowers at nodes. Once branching also occurs at the node, the flower will grow above the branch before producing a flower. Flowers grow very bulbous, almost spherical. Leaves surrounding the buds radiate and are more present around apical buds. |
| Proportion of female plants | 50% grown from seed, normal dioecious plant |
| Inflorescence Position | Above. |
| Flower arrangement | Overlapping, congested, individual flowers grow in spherical formation. Flowers are stacked or clustered at maturity. |
| Number of Flowers per plant | Hundreds to thousands per plant. |
| Flower shape | Has mostly radial symmetry with leaves growing all around the flowers. Because of its separation from other buds, it generally grows spherically. |
| Flower (individual pistillate) length | 7-13 mm |

TABLE IV-continued

| Inflorescence | |
|---|---|
| Flower (compound cyme) diameter | 2-11 cm |
| Corolla | No defined corolla. |
| Corolla Color (RHS number) | N/A |
| Bract shape | Broad /rounded base with long, tapering apex. Longer and more prominent than offspring. |
| Bract color (RHS number) | 150A |
| Bracteole shape (general description) | Same as bract, further enclosed in flower so hard to identify without dissection. |
| Bracteole color (RHS number) | 150A |
| Calyx Shape (general description) | Not Present |
| Calyx color (RHS number) | N/A |
| Stigma shape | Ovate shape with broad base and tapering apex with 1-2 styles protruding. Generally smaller and broader than offspring. |
| Stigma length | 5-8 mm |
| Stigma color (RHS number) | 150A |
| Trichome shape | Capitate stalked gland, stalk is shorter than offspring. In mature plants grow on flowers and petioles. |
| Cystolithic non-glandular | Present on leaves. |
| Trichome color (RHS number) | Opaque/white but changes with maturity/when ready to harvest. |
| Terminal Bud shape | More radial symmetry from leaves growing without obstruction from stem. |
| Terminal Bud color (RHS number) | 145B to 145D |
| Pedicle | Present but shorter than the offspring |
| Staminate shape | N/A |
| Sepal color (RHS number) | N/A |
| Pollen description | N/A |
| Seed description | Seeds are 2-3 mm in length. The seeds have vertical lines along the sides of the seed but only 3-5 per seed. The seed is a light brown with white lines that look like veins between some of the vertical lines. |
| Marbling of seed | There is no marbling. |
| Petal description | N/A |

TABLE V

| Other Characteristics | |
|---|---|
| Characteristics | New Variety ('NaCl') |
| Time period and condition of flowering/blooming | Flower production is initiated when plants are taken from vegetative growth at 24-hour light and switched to 12 hours of light followed by 12 hours of dark during what would be the nocturnal period. Flowers are mature typically 75 days after flowering light cycle is initiated. |
| Proportion of hermaphrodite plants | None |

TABLE V-continued

| Other Characteristics | |
|---|---|
| Hardiness of plant | Salt and drought tolerant and grows well on several different, diverse nutrient formulas. Also tolerant to clay soil and small rootzone conditions (i.e., indoor pots). |
| Breaking action | Above average, very sturdy. |
| Seed Shattering | Minimal |
| Root rate after cutting/cloning | Has exhibited 100% success at new root development after cloning. Adventitious roots appear at 10-14 days. |
| Total THC and CBD Content at harvest maturity | Total CBD content: 12.6%<br>Total THC content: 0.53%<br>Total CBD:THC Ratio: 25:1 |
| **Characteristics** | **Parental Variety (CC) (Female Plant)** |
| Time period and condition of flowering/blooming | Flower production is initiated when plants are taken from vegetative growth at 24-hour light and switched to 12 hours of light followed by 12 hours of dark during what would be the nocturnal period. Flowers mature typically 75 days after the flowering light cycle is initiated. |
| Proportion of hermaphrodite plants | None |
| Hardiness of plant | Tolerant to salty soil and drought conditions. |
| Breaking action | Above average, very sturdy. |
| Seed Shattering | Minimal |
| Root rate after cutting/cloning | Has exhibited 100% success at new root development after cloning. Adventitious roots appear at 10-14 days. |
| Total THC and CBD Content at harvest maturity | Total CBD content: 15.5%<br>Total THC content: 0.77%<br>Total CBD:THC Ratio: 20:1 |

The botanical descriptions provided are generalizing from plants grown indoors in controlled conditions and outdoors in high salinity soil. Total potential cannabinoid content is measured using a formula to account for decarboxylation of the acidic forms to allow for more accurate estimation. The formulas used are provided for convenience:

$$\text{Total THC}=\text{THC}+(\text{THCA}*(0.877));$$

$$\text{Total CBD}=\text{CBD}+(\text{CBDA}*(0.877)).$$

The G feminized father, similar to its offspring, has alternate, palmately compound leaves with 3-5 leaflets when immature and up to 7 at maturity. The leaflets have jagged serrate margins with the tooth apex angled towards the leaflet apex and about 20-28 teeth per leaflet. The leaves with the petiole are about 11-15 cm long and the petiole alone is about 3-4 cm long. The middle largest leaflet is about 8-11 cm long and 3-4 cm wide for about a 3:1 length to width ratio. The father has significantly broader leaflets than 'NaCl' which likely resembles the leaf structure more of the mother. Generally, the GFF variety has the potential to produce 11% CBD and 0.5% THC which is less than 'NaCl'. Other physical differences are present between 'NaCl' and the GFF father due to the different appearances between male and female sex organs since the father is a feminized female. For example, both feminized and non-feminized female plants have thick buds at the apex of the stems, however, where a non-feminized female produces buds, a feminized female produces pollen sacs. The other structural differences are prominent due to the difference in the two genotypes with GFF resembling more of an indica dominant plant with broad shorter leaflets and resembling that in growth. 'NaCl' is more similar to a *sativa* dominant plant because it grows much skinnier and taller than the GFF and is more structurally similar to the CC mother than the GFF father.

When compared to the CC mother, 'NaCl' is generally more robust and hardier and is larger by about 20%. 'NaCl' has more leaflets and serrations with 7-9 leaflets and 34-42 teeth per leaflet through maturity where the CC has only 5-7 leaflets with 23-25 teeth per leaflet. Additionally, the 'NaCl' is a much more resilient plant compared to the CC mother which will become incredibly stressed in wet or humid environments and only thrives in desert climates. 'NaCl' did inherit its tolerance to high salinity from its CC mother but was improved upon in further breeding making it even more resilient. CC is much more temperamental and harder to manage indoors, but will do better outside. 'NaCl' on the other hand will exhibit impressive growth whether grown inside or outside. The flowers on 'NaCl' are also much more elongated and denser than CC which has more radial symmetry and is much more spherical in appearance than cylindrical.

When compared to the *Cannabis sativa* Hemp variety 'CW24', the 'NaCl' grows generally taller and is more resilient. 'CW24' was one of the initial 10 mothers tested in high salt soil but was not nearly as stress resistant or tolerant of the poor soil conditions compared to the CC mother. The same lack of resilience can be seen when comparing 'CW24' to 'NaCl'. The leaves have generally fewer leaflets on 'CW24' and are often narrower with fewer serrations with 19-29 teeth per leaflet compared to 34-42 on 'NaCl'. Additionally, the 'NaCl' has larger internodes throughout the plant which results in more spread buds that cluster only near the apical ends of branches, where 'CW24' has overlapping buds throughout the branches. The flowers on 'CW24' are more of a compressed oval shape compared to the more cylindrical appearance with a pointed apex found on 'NaCl'. Mature 'NaCl' flowers also have a peppery and fruity aroma compared to the earthy aroma of 'CW24'. 'NaCl' has a CBD:THC ratio of 25:1 with CBD at about 13% compared to 'CW24' of 23:1 with CBD only about 5-8%.

Growth conditions:

*Vegetative growth period.*—24-hour light continuously. 78° F. and 60% humidity.

*Flower production period.*—12-hour light followed by 12-hour dark cycle repeating. 78° F. and 45% humidity.

Outdoor growth: 'NaCl' was developed by being grown outdoors on a farm located in Sonoma County, Calif. that has high salinity soil due to annual flooding from its proximity to a saltwater slough. The plants were planted as 30-day clones late in the season, Aug. 13, 2020, resulting in an earlier flowering and smaller plants. The mother strain was also tested on this farm, but all breeding was done indoors in a controlled environment. The 'NaCl' plant has the potential to reach a maximum of 8 to 10 feet tall and 6 to 8 feet wide. Compared to indoor growth, the plant will be more robust and have a faster growth rate with wider leaves. When grown outdoors, the father, G, variety will reach 6 to 8 feet tall and 6 to 7 feet wide and the mother, CC, variety will reach 8 to 10 feet tall and 6 to 8 feet wide.

Vigor: Exhibits most vigorous and rapid growth, showing little stress in most growing environments.

Coloration: Changes in coloration occur with nutrient deficiencies or other variation in growing maintenance.

The invention claimed is:

1. A new and distinct cultivar of hemp plant, named 'NaCl', as herein described and illustrated.

* * * * *